(12) United States Patent
Burnes et al.

(10) Patent No.: US 7,445,522 B2
(45) Date of Patent: Nov. 4, 2008

(54) ELECTRODE CONNECTOR

(75) Inventors: Lee Burnes, Wilbraham, MA (US); Scott Coggins, Palmer, MA (US); Dave Selvitelli, Suffield, CT (US); Mark Tauer, Belchertown, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 11/634,028

(22) Filed: Dec. 5, 2006

(65) Prior Publication Data

US 2008/0132773 A1    Jun. 5, 2008

(51) Int. Cl.
*H01R 4/28* (2006.01)

(52) U.S. Cl. .................. 439/725; 439/859; 439/729; 439/909

(58) Field of Classification Search ............ 439/725, 439/309, 909, 859, 729
See application file for complete search history.

(56) References Cited

U.S. PATENT DOCUMENTS

| | | |
|---|---|---|
| 3,606,881 A | 9/1971 | Woodson |
| 3,805,769 A | 4/1974 | Sessions |
| 3,895,635 A | 7/1975 | Justus et al. |
| 4,026,278 A | 5/1977 | Ricketts et al. |
| 4,112,941 A | 9/1978 | Larimore |
| 4,165,141 A | 8/1979 | Williams et al. |
| 4,166,465 A | 9/1979 | Esty et al. |
| 4,253,721 A | 3/1981 | Kaufman |
| 4,304,453 A | 12/1981 | Grunwald |
| 4,632,121 A | 12/1986 | Johnson et al. |
| 4,685,467 A * | 8/1987 | Cartmell et al. ............. 600/385 |
| 4,842,557 A * | 6/1989 | Muz ............................ 439/857 |
| 5,390,883 A * | 2/1995 | Songhurst .................. 248/74.3 |
| 5,546,950 A * | 8/1996 | Schoeckert et al. ......... 600/508 |
| 6,023,631 A * | 2/2000 | Cartmell et al. ............. 600/372 |
| 6,487,430 B1 * | 11/2002 | Henderson et al. .......... 600/394 |

FOREIGN PATENT DOCUMENTS

EP    0 247 560    12/1987

OTHER PUBLICATIONS

International Search Report EP 07 25 4692 dated Mar. 27, 2008.

* cited by examiner

*Primary Examiner*—Renee S Luebke
*Assistant Examiner*—Vanessa Girardi
(74) *Attorney, Agent, or Firm*—Carter, DeLuca, Farrell & Schmidt LLP

(57) ABSTRACT

A biomedical electrode connector for coupling with a biomedical electrode of the type including an electrode base and a male terminal projecting from the electrode base is provided. The electrode connector includes a jacketed housing having an internal cavity with an electrical contact material adapted for electrical coupling relation with an electrical lead wire. The jacketed housing includes a lower member positionable adjacent the electrode and having internal surface portions defining a keyhole slot therein. The keyhole slot has a first slot portion defining a first internal dimension to permit passage of the male terminal of the electrode for reception within the internal cavity, and a second slot portion defining a second internal dimension less than the first dimension whereby, upon traversing movement of the male terminal within the internal cavity, the male terminal is secured within the internal surface portions defining the second slot portion to thereby electrically couple the electrode with the electrode connector.

25 Claims, 5 Drawing Sheets

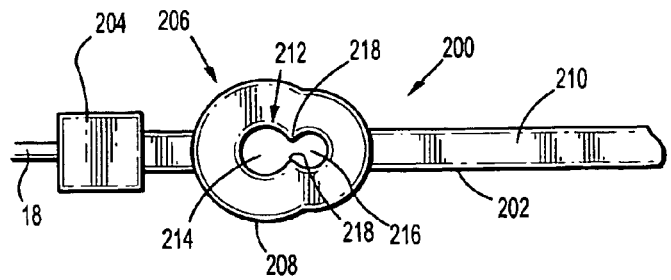
FIG. 12
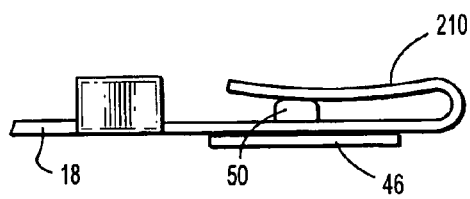
FIG. 13
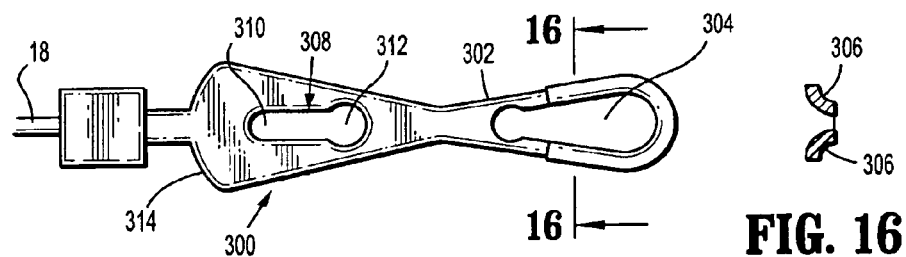
FIG. 14     FIG. 16
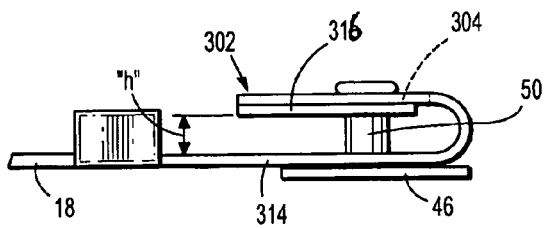
FIG. 15

ELECTRODE CONNECTOR

BACKGROUND

1. Technical Field

The present disclosure generally relates to biomedical electrodes and, in particular, relates to a biomedical electrode connector for effecting an electrical connection between an electrode on a patient and an electro-medical device.

2. Discussion of Related Art

Biomedical electrodes are commonly used in diagnostic and therapeutic medical applications including, e.g., electrocardiograph procedures, maternal and/or fetal monitoring, and a variety signal based rehabilitative procedures. A conventional biomedical electrode is secured to the skin of a patient via an adhesive and incorporates a male terminal or pin which projects from an electrode base. An electrical cable in communication with the electro-medical device incorporates a female terminal which is connected to the male terminal to complete the electrical circuit between the electrode and the electro-medical device. Various mechanisms for connecting the female terminal to the male terminal are known including "snap on" connections, "pinch clip" arrangements, "twist on" couplings or magnetic couplings. Many, if not all, currently available biomedical electrodes are disposable, i.e., intended to be discarded after a single use.

SUMMARY

Accordingly, the present disclosure is directed to a biomedical electrode connector for coupling with a biomedical electrode of the type including an electrode base and a male terminal projecting from the electrode base. The electrode connector includes a jacket that covers and electrically insulates a housing having an internal cavity with an electrical contact material adapted for electrical coupling relation with an electrical lead wire. The jacketed housing includes a lower member positionable adjacent the electrode and having internal surface portions defining a keyhole slot therein. The keyhole slot has a first slot portion defining a first internal dimension adapted to permit passage of the male terminal of the electrode for reception within the internal cavity, and a second slot portion defining a second internal dimension less than the first dimension whereby, upon traversing movement of the male terminal within the internal cavity, the male terminal is secured within the internal surface portions defining the second slot portion to thereby electrically couple the electrode with the electrode connector.

The jacketed housing may include an internal ramp at least partially disposed within the internal cavity adjacent the second slot portion whereby, upon traversing movement of the male terminal toward the second slot portion, the internal ramp engages the male terminal to drive the male terminal into contacting relation with the electrical contact material to facilitate the electrical coupling with the electrical contact material. The lower member may include the internal ramp. The jacketed housing may include an upper member, where the upper member has the internal ramp.

The jacketed housing may include at least one flexible locking element extending within the keyhole slot. The at least one locking element is adapted to flex during the traversing movement of the male terminal toward the second slot portion to permit passage of the male terminal therewithin, and further adapted to return to a preflex state to engage the male terminal to facilitate retention thereof within the second slot portion. The jacketed housing may include first and second opposed locking elements.

In one embodiment, the jacketed housing includes an upper member having the electrode contact material associated therewith. In the alternative or in addition thereto, the lower member may have the electrical contact material associated therewith. The lower member may include a spring clip. The spring clip is adapted to engage the male terminal to electrically couple the electrode with the electrode connector. The spring clip may include an elongated opening in general alignment with the keyhole slot and being adapted for reception of the male terminal. The spring clip is adapted to engage the male terminal and normally bias the male terminal within the jacketed housing. The elongated opening of the spring clip may define a first opening portion in general alignment with the first slot portion of the keyhole slot and having an internal dimension greater than the male terminal, and a second opening portion in general alignment with the second slot portion and having an internal dimension less than the male terminal whereby, upon traversing movement of the male terminal from the first slot portion to the second slot portion, the male terminal is engaged by clip portions defining the second slot portion into electrical contact with the electric contact material.

In another embodiment, a biomedical electrode lead set assembly includes a cable including at least one electrical lead wire, a device connector at one end of the one electrical lead wire for coupling to a biomedical device and an electrode connector at the other end of the one electrical lead wire for coupling with an electrode terminal of a biomedical electrode. The electrode connector includes a lower member positionable adjacent the electrode and having internal surface portions defining a keyhole slot therein. The keyhole slot has a first slot portion defining a first internal dimension and a second slot portion defining a second internal dimension less than the first internal dimension. The jacketed housing is positionable over the biomedical electrode with the electrode terminal being received within the first slot portion and being slidable relative to the biomedical electrode whereby the electrode terminal traverses the keyhole slot to be received within the second slot portion and retained therein through cooperative engagement of the electrode terminal with housing portions defining the second slot portion to thereby mechanically and electrically couple the electrode with the electrode connector.

A plurality of electrode lead wires and associated electrode connectors may be provided. The cable may be a lead set cable. The electrode lead wires may be individually separable from the lead set cable. A pad may be mounted to the cable and adapted to slide along the cable for positioning adjacent to a predetermined body position. The pad has a material facilitating attachment of the pad to the predetermined body position to thereby secure the cable relative to a patient. The material may include a pressure sensitive adhesive coating or an adhesive hydrogel.

The electrode connector may include a jacketed housing with the lower member being mounted within the jacketed housing.

Alternatively, the electrode connector may include an upper member having an elongated slot therethrough in general alignment with the keyhole slot of the lower member to receive the electrode terminal to facilitate securement of the electrode terminal within the electrode connector. The lower membrane and the upper membrane may define a resilient clip.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 12 is a top plan view of an alternate embodiment of an electrode connector for use with the electrode lead set assembly and depicted in a preformed condition;

FIG. 13 is a side plan view of the electrode connector of FIG. 12 connected to a biomedical electrode;

FIG. 14 is a top plan view of another alternate embodiment of an electrode connector for use with the electrode lead set assembly and depicted in a preformed condition;

FIG. 15 is a side plan view of the electrode connector of FIG. 14 connected to a biomedical electrode; and FIG. 16 is a cross-sectional view of the electrode connector taken along the lines 16-16 of FIG. 14.

DETAILED DESCRIPTION OF THE PREFERRED EMBODIMENT(S)

The exemplary embodiments of the electrode lead set assembly disclosed herein is discussed in terms of use of the lead set assembly in performing a surgical, diagnostic or therapeutic procedure in collecting or delivering electrical signals relative to a subject. Such procedures are inclusive of, but, not limited to, electrocardiograph procedures, maternal and/or fetal monitoring, and a variety of signal based rehabilitative procedures. However, it is envisioned that the present disclosure may be employed with many applications including surgical, diagnostic and related treatments of diseases, body ailments, of a subject.

In the discussion that follows, the term "subject" refers to a human patient or other animal. The term "clinician" refers to a doctor, nurse or other care provider and may include support personnel.

Figure 1:
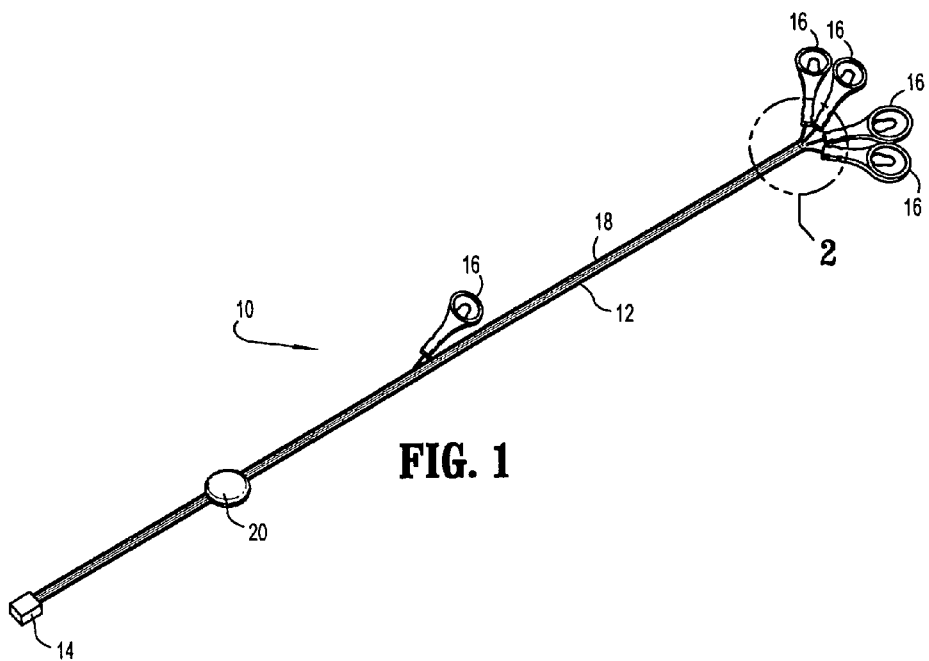
FIG. 1 is a perspective view of a biomedical electrode lead set assembly in accordance with the principles of the present disclosure illustrating the lead set cable, adjustable attachment pad and electrode connectors attached to the lead set cable.

Referring now to the drawings wherein like components are designated by like reference numerals throughout the several views, FIG. 1 illustrates, in perspective view, the electrode lead set assembly 10 in accordance with the principles of the present disclosure. Electrode lead set assembly 10 includes lead set cable or web 12, device connector 14 at one end of the lead set cable 12 and a plurality of electrode connectors 16 some of which are at the other end of the lead set cable 12. Lead set cable 12 includes a plurality of encased and insulated lead wires 18 disposed in side by side relation. Insulated lead wires 18 may be EMI/RF shielded. Lead set cable 12 may be a ribbon cable, a multi-conductor shielded cable or any other cable suitable for transmitting electrical signals.

Figure 2:
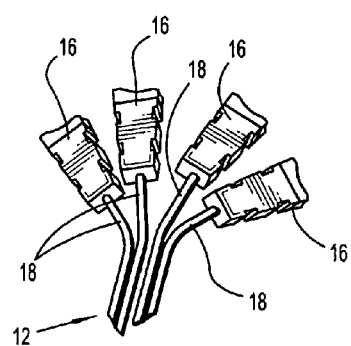
FIG. 2 is a partial perspective view of the area of detail identified in FIG. 1 illustrating the lead wires of the lead set cable and the electrode connectors illustrating the tear away capabilities of the lead wires.

As depicted in FIG. 2, each lead wire 18 is independently separable from an adjacent lead wire 18 to facilitate placement of a respective electrode connector 16 at a predetermined body location, to thereby permit customization of the lead set assembly 10 for each subject, i.e., each lead wire 18 may be independently separable from lead set cable 12. In FIG. 2, portions of electrode connector 16 are shown removed. In one embodiment, lead wires 18 are attached via their insulated covers and, are separable along respective lines of juncture of the insulated covers of adjacent lead wires 18. In another embodiment, lead set cable 12 includes a flexible substrate or backing which is desirably separable to separate lead wires 18 along a major portion of their length. Individual lead wires 18 of lead set cable 12 may be varied in length to permit placement of an individual electrode connector 16 at a target site, e.g. across the chest or abdomen, to permit collection or delivery of biomedical signals at these locations. FIG. 1 illustrates one individual lead wire 18 which is approximately ½ the length of the remaining lead wires 18.

Medical device connector 14 may be any suitable connector adapted for connection to a medical device such as an electrocardiogram apparatus, fetal or maternal monitoring apparatus or a signal generator adapted to transmit electrical impulses or signals for therapeutic reasons to the patient. One suitable medical device connector may be a modular connector similar to those used for Registered Jacks Including RJ14, RJ25, and RJ45 connectors.

Figure 3:
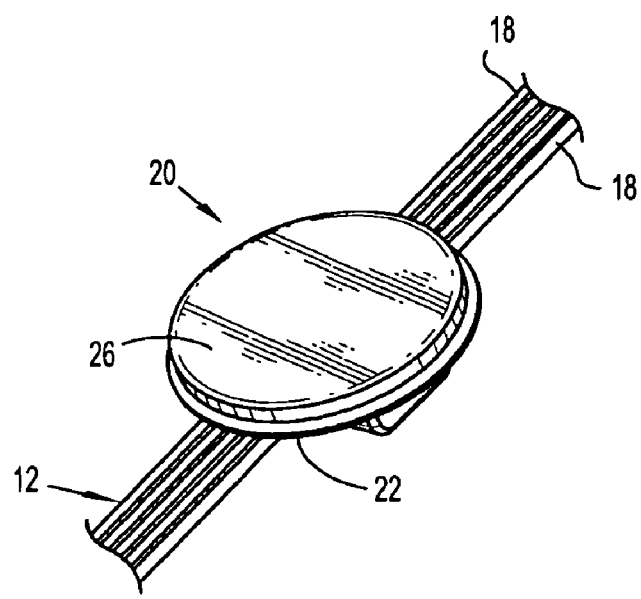
FIGS. 3-4 are top and bottom perspective views of the adjustable attachment pad.
Figure 4:
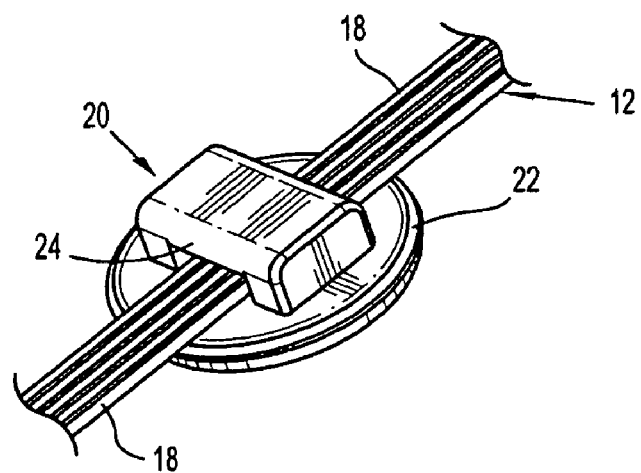

Referring now to FIGS. 3-4, in conjunction with FIG. 1, lead set assembly 10 may further include an attachment pad 20 mounted about lead set cable 12. In one embodiment, attachment pad 20 includes base 22 having a closed loop 24 which receives lead set cable 12. On the other side of attachment pad 20 is a flexible attachment element 26 which is adapted for positioning adjacent the body tissue. Flexible attachment element 26 may have a suitable material on its tissue contacting surface such as a pressure sensitive adhesive coating or an adhesive hydrogel which facilitates securing of attachment pad 20 to the subject. Attachment pad 20 is slidably mounted relative to lead set cable 12 by virtue of the lead set cable 12 sliding through closed loop 24 of base 22. With this arrangement, attachment pad 20 may be selectively positioned and attached to a subject at a desired location to thereby facilitating securement of lead set cable 12 and lead set assembly 10 relative to the subject.

Figure 5:
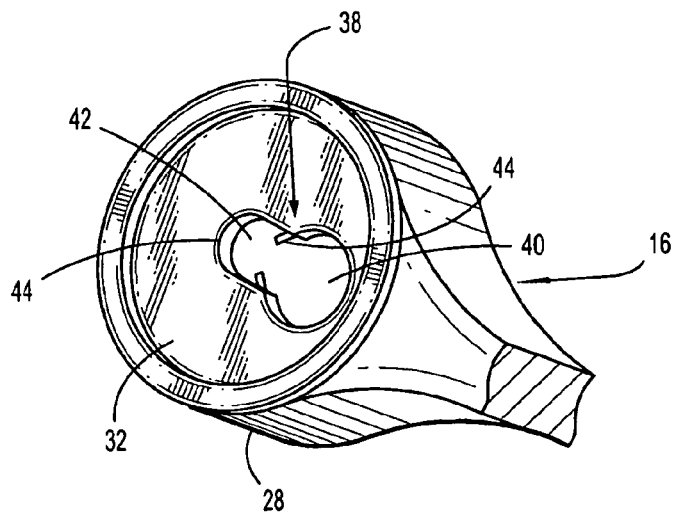
FIG. 5 is a perspective view of one of the electrode connectors.
Figure 6:
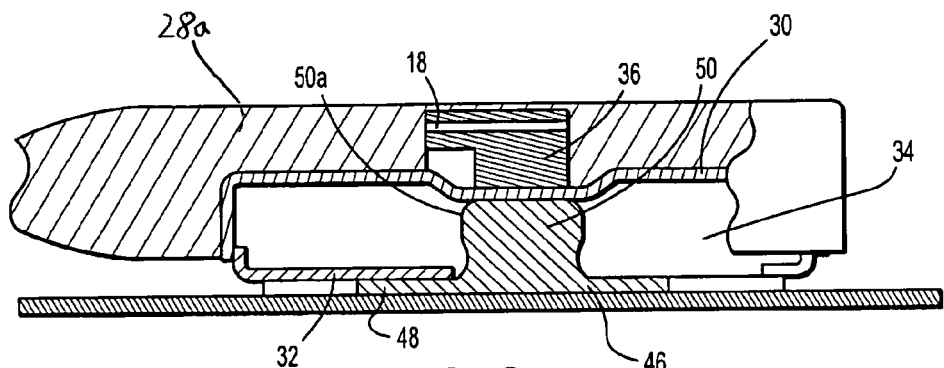
FIG. 6 is a side cross-sectional view of the electrode connector of FIG. 5.
Figure 7:
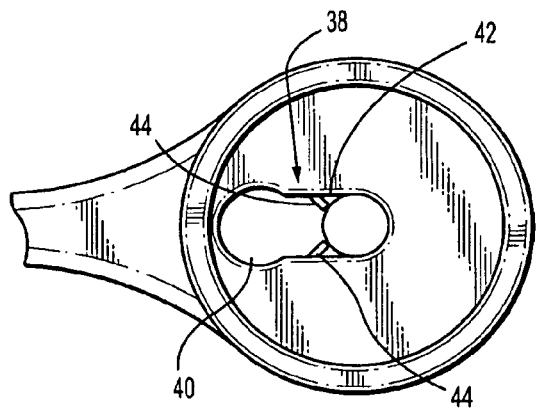
FIG. 7 is a plan view with portions cut-away illustrating the electrode terminal retained within the electrode connector of FIG. 5.
Figure 8:
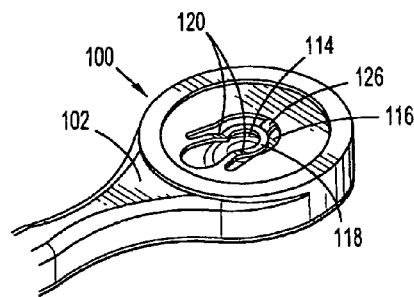
FIG. 8 is a perspective view of an alternate embodiment of an electrode connector for use with the electrode lead set assembly.
Figure 9:
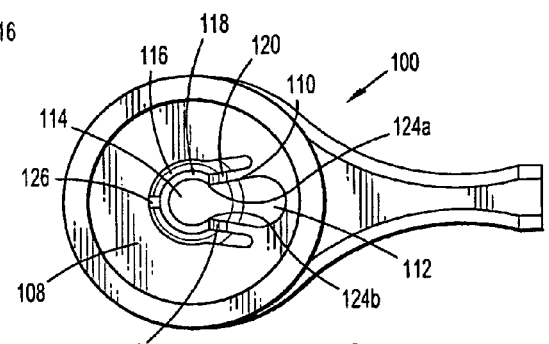
FIG. 9 is a plan view of the electrode connector of FIG. 8.
Figure 10:
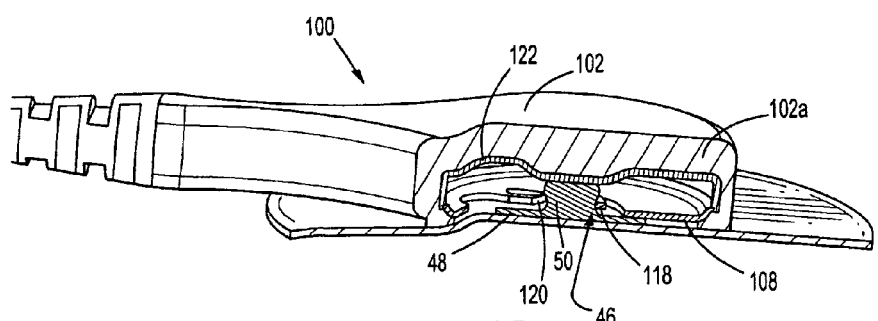
FIG. 10 is a perspective view with portions cut-away of the electrode connector of FIG. 8.
Figure 11:
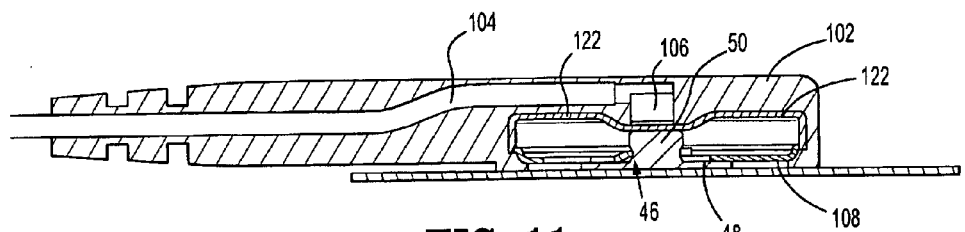
FIG. 11 is a side cross-sectional view of the electrode connector of FIG. 8.

Referring now to FIGS. 5-7, electrode connector 16 of lead set assembly 10 will be discussed. Electrode connector 16 includes jacketed housing 28 having upper member 30 and lower member 32, and defining internal cavity 34 therebetween. Jacketed housing 28 includes an external jacket 28a of a non-conducting material, e.g., an over molded polymer which electrically insulates the subject from the conductive element(s) within the jacketed housing 28. In FIG. 6, a portion of external jacket 28a is removed. Upper member 30 and lower member 32 may be separate components attached to each other by conventional means or may be a single monolithically formed component to form a conductive element of the jacketed housing 28. Upper member 30 of jacketed housing 28 has lead wire terminal 36 which is electrically connected to a respective lead wire 18. Lower member 32 of jacketed housing 28 defines keyhole slot 38 extending therethrough and in communication with internal cavity 34 of the jacketed housing 28. Keyhole slot 38 includes first slot portion 40 and second slot portion 42. First slot portion 40 defines an internal dimension or diameter which is greater than the corresponding internal dimension or diameter of second slot portion 42. Lower member 32 furthers include a plurality of flexible locking elements 44 at the juncture of first and second slot portions 40, 42. Locking elements 44 are adapted to flex inwardly, but, have sufficient resiliency to return to their initial position depicted in FIG. 7. In this regard, locking elements 44 may be formed of any of flexible springlike material including stainless steel, titanium, or a polymer material.

Electrode connector 16 is adapted for connection to biomedical electrode 46. As best depicted in FIG. 6, biomedical electrode 46 incorporates electrode flange or base 48 and male stud or terminal 50 extending in transverse relation to the electrode base 48. Male terminal 50 may have a bulbous arrangement whereby the upper portion 50a of the male terminal 50 has a greater cross-sectional dimension than a lower portion of the male terminal 50. A pressure sensitive adhesive coating and an adhesive hydrogel (not shown) may be applied to tissue contacting surface of electrode base 48 to enhance the electrical connection to the subject to receive/transmit the biomedical signals to/from the subject. Any commercially available biomedical electrode 46 having an upward extending male terminal or pin 50 may be utilized.

In use of electrode lead set assembly 10, the lead set assembly 10 is placed adjacent the body of the subject. Biomedical electrodes 46 are positioned on the body as deemed necessary and secured to the body with the use of a pressure sensitive adhesive or an adhesive hydrogel or the like. Each electrode connector 16 is then positioned with respect to an associated electrode 46. As appreciated, lead wires 18 connected to respective biomedical electrodes 46 may be separated from lead set cable 12 to permit selective individual positioning of the lead wire 18 for connection to the electrode 16. An electrode connector 16 is positioned such that male terminal 50 of biomedical electrode 46 is received within first slot portion 40 of keyhole slot 38 of lower member 32. Thereafter, electrode connector 16 is slid relative to biomedical electrode 46 whereby male terminal 50 traverses first slot portion 40 to be received within second slot portion 42 of keyhole slot 38. During this traversing movement, locking elements 44 flex inwardly to permit passage of male terminal 50 whereby upon clearance of the male terminal 50, locking elements 44 return to their initial position depicted in FIG. 7. In this position, contacting surfaces of lead wire terminal 36 contacts the upper surface of male terminal 50 of biomedical electrode 46 thereby completing the electrical circuit. Thus, with this arrangement of keyhole slot 38 of electrode connector 16, minimal or no downward force is required to secure electrode connector 16 to biomedical electrode 40. Accordingly, the potential for undesired movement of biomedical electrode 46 is minimized thereby maintaining the integrity of the procedure and minimizing the infliction of pain on the subject's chest or abdomen.

FIGS. 8-11 illustrate an alternate embodiment of the electrode connector. Electrode connector 100 includes jacketed housing 102 having lead wire 104 extending to connect to lead wire terminal 106 within the jacketed housing 102. Jacketed housing 102 has an external jacket 102a of insulative or non-conductive material. Lower member 108 of jacketed housing 102 defines a keyhole slot 110 similar to the keyhole slot described hereinabove in connection with FIGS. 5-7. In particular, keyhole slot 110 includes first slot portion 112 defining a relatively large internal dimension or diameter and second slot portion 114 defining an internal dimension or diameter which is less than that of first slot portion 112. Lower member 108 further includes arcuate relief opening or cut-out 116 circumscribing at least second slot portion 114 and, preferably, extending along a peripheral area of first slot portion 112. This arrangement thereby defines an electrode contact tab 118 within lower member 108 extending in cantilever relation with respect to jacketed housing 102. In one embodiment, contact tab 118 has opposed internal ramp surfaces 120 generally at the juncture of first and second slot portions 112, 114. Ramp surfaces 120 are obliquely arranged relative to lower member 108, and are adapted to provide an upward force to male terminal 50 of biomedical electrode 46 as the male terminal 50 traverses first slot portion 112 to be received within second slot portion 114 of keyhole slot 110. Ramp surfaces 120 are configured and dimensioned to draw male terminal 50 of biomedical electrode 46 into contact with a contact surface of lead wire terminal 106 thereby ensuring a well-established or effective electrical contact between lead wire terminal 106 and electrode 46. In addition, ramp surfaces 120 draw male terminal 50 into jacketed housing 102 in a manner to cause electrode base or flange 48 to electrically contact lower member 108. Thus, by virtue of the arrangement of ramp surface 120, contact between tab 118 and biomedical electrode 46 is established at least along the following locations: 1) between the upper surface of male terminal 50 of electrode 46 and upper member 122 within jacketed housing 102; 2) between the outer or barrel surface of male terminal 50 and contact tab 118 (i.e., the internal edge or surface defining second slot portion 114; and 3) between electrode base 48 and lower member 108.

In this embodiment, electrode connector 100 is devoid of locking elements. Rather, male terminal 50 of electrode 46 is retained within second slot portion 114 of electrode contact tab 118 due to the inherent resiliency of the material of fabrication of lower member 108. In one embodiment, the juncture area 124a, 124b between first and second slots portion 112, 114 is resiliently flexible and defines a dimension which is less than the dimension of male terminal 50 of electrode 46. Juncture area 124a, 124b may flex outwardly as provided by arcuate relief opening 116 to permit passage of male terminal 50, and then return under it own resilient characteristics to the initial position depicted in FIG. 9 securely engaging male terminal 50 of electrode in electrical contact therewith. As a further alternative, lower member 108 may have an arcuate reinforcement area or tab 126 extending between electrode contact tab 118 and lower member 108. Reinforcement tab 126 may desirably add some strength or rigidity along this area to ensure male terminal 50 is securely engaged within second slot portion 114. Reinforcement tab 126 may be any suitable relative rigid material integrated into lower member 108.

FIGS. 12-13 illustrate an alternate embodiment for the conductive portions of the electrode connector 200. Various metallic stampings are envisioned; FIG. 12 illustrates electrode connector 200 in a pre-formed condition. In accordance with this embodiment, electrode connector 200 includes spring clip 202 which may be encased within an insulating jacket as hereinbelow discussed. Spring clip 202 includes lead terminal 204 which connects to a lead wire 18. Depending from lead terminal 204 is connector portion 206 having base 208 and electrode contact tab 210. Base 208 defines modified keyhole slot 212 defining first slot portion 214 and second slot portion 216. First slot portion 214 defines an internal dimension or diameter greater than the internal dimension or diameter of second slot portion 216. In an operative position, electrode contact tab 210 is bent upon itself to overlap keyhole slot 212 as depicted in FIG. 13. In this position, electrode contact tab 212 contacts the upper surface of male terminal 50 of electrode 46 to effect electrical coupling of connector 200 with the electrode 46.

In use, spring clip 202 in the arrangement of FIG. 13 is positioned over male terminal 50 to be received within first slot portion 214 of keyhole slot 208. Spring clip 202 is slid relative to male terminal 50 whereby the male terminal 50 traverses the keyhole slot 212 for reception within second slot portion 216. In one embodiment, the juncture of first and second slot portions 214, 216 defines opposed internal shelves 218 which define a dimension therebetween less than the dimension of male terminal 50. Upon traversing movement of male terminal 50 within keyhole slot 212, shelves 218 are biased outwardly to permit passage of the male terminal 50 while returning under their resilient characteristics to the normal position of FIG. 12 thereby retaining the male terminal 50 within the second slot portion 216. With male terminal 50 within second slot portion 216, electrode contact tab 210 contacts the upper surface of male terminal 50 thereby establishing the electrical coupling between the electrode 46 and electrode connector 46.

FIGS. 14-16 illustrate another embodiment for the conductive portion of an electrode connector 300. FIG. 14 illustrates electrode connector 300 in a pre-formed condition. Connector 300 is similar to connector 200 discussed in connection with FIGS. 12-13. Electrode contact tab 302 defines an elongated opening 304 having a dimension which gradually increases in linear manner. In addition, the interior portions 306 defining elongated opening 304 are rolled or deflected upwardly as depicted in FIG. 16. FIG. 15 illustrates electrode contact tab 302 rolled over in general alignment with keyhole slot 308. Thus, in use, male terminal 50 is received within keyhole slot 308, specifically, within first slot portion 310 and within elongated opening 304 of electrode contact tab 302. Thereafter, electrode connector 300 is moved linearly relative to electrode 46 whereby male terminal 50 of electrode 46 traverses keyhole slot 308 for reception within second slot portion 312 and the more narrow portion of elongated opening 304 of electrode contact tab 302. The more narrow portion of elongated opening 304 serves to restrict movement of electrode connector 300 relative to male terminal 50. In addition, the rolled or deflected interior portions 306 facilitate passage of male terminal 50 through elongated opening 304. Furthermore, electrode contact tab 302, by virtue of its inherently resiliency and the arrangement of deflected interior portions 306, tends to engage and lift the upper bulbous portion 50a of male terminal 50 of electrode 46 in an upward direction to cause flange 48 of electrode 46 to engage lower or base member 314 of the electrode contact tab 302 in electrical contacting relation to thereby ensure a proper electrical connection, e.g., at two locations. It is appreciated that the height or distance "h" between lower member 314 and upper member 316 is selected to be at least equal to or greater than the distance between electrode flange 48 and bulbous portion 50a of male terminal 50 such that when electrode 46 is secured within electrode contact tab 302, the upper member 316 will normally bias electrode 46 in an upward direction to facilitate establishing of the desired electrical contact.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A biomedical electrode connector assembly for coupling with a biomedical electrode including an electrode base and a male terminal projecting from the electrode base, the electrode connector comprising:
   a connector housing having electrical contact material adapted to establish an electrical coupling relation with an electrical lead wire, the connector housing including:
      a lower member adapted to be positioned adjacent the electrode and having internal surface portions defining a terminal slot therein, the terminal slot having a first slot portion defining a first internal dimension adapted to receive the male terminal of the electrode and a second slot portion defining a second internal dimension less than the first internal dimension; and
      a flexible locking element depending at least radially inwardly relative to the terminal slot;
   whereby, upon traversing movement of the male terminal within the terminal slot from the first slot portion to the second slot portion, the flexible locking element is adapted to flex toward the internal surface portions to permit passage of the male terminal and, thereafter, return toward a preflex state to engage the male terminal to facilitate retention of the male terminal within the second slot portion.

2. The biomedical electrode connector assembly according to claim 1 wherein the connector housing includes first and second opposed locking elements, each of the first and second locking elements depending at least radially inwardly relative to the terminal slot.

3. The biomedical electrode connector assembly according to claim 1 wherein the connector housing includes an upper member, the upper member having the electrode contact material associated therewith.

4. The biomedical electrode connector assembly according to claim 1 wherein the lower member has the electrical contact material associated therewith.

5. The biomedical electrode according to claim 1 wherein the flexible locking element is connected to the lower member.

6. The biomedical electrode connector assembly according to claim 1 wherein the connector housing includes an upper member adapted to engage the male terminal to electrically couple the electrode with the electrode connector.

7. The biomedical electrode connector assembly according to claim 6 wherein the upper member includes tab portions of a contact tab, the tab portions define an elongated opening in general alignment with the terminal slot and adapted to at least partially receive the male terminal.

8. The biomedical electrode connector assembly according to claim 7 wherein the elongated opening of the tab portions defines a first opening portion having an internal dimension greater than the male terminal, and a second opening portion having an internal dimension less than first dimension whereby, upon traversing movement of the male terminal from the first slot portion to the second slot portion, the male terminal is electrically engaged with the electric contact material.

9. The biomedical electrode connector assembly according to claim 1 including:
   a cable including at least one electrical lead wire for electrical coupling with the electrical contact material of the connector housing; and a device connector at one end of the one electrical lead wire for coupling to a biomedical device.

10. The biomedical electrode connector assembly according to claim 9 including a plurality of electrode lead wires and associated electrode connectors.

11. The biomedical electrode connector assembly according to claim 10 wherein the cable is a lead set cable.

12. The biomedical electrode connector assembly according to claim 11 wherein the electrode lead wires are individually separable from the lead set cable.

13. The biomedical electrode connector assembly according to claim 9 including a pad mounted to the cable and adapted to slide along the cable for positioning adjacent a predetermined body position, the pad having a material facilitating attachment of the pad to the predetermined body position to thereby secure the cable relative to a patient.

14. The biomedical electrode connector assembly according to claim 13 wherein the material includes an adhesive material.

15. A biomedical electrode connector for coupling with a biomedical electrode including an electrode base and a male terminal projecting from the electrode base, the electrode connector comprising:
a connector housing having electrical contact material adapted for electrical coupling with an electrical lead wire, the connector housing including:
a base member adapted to be positioned adjacent the electrode and having internal surface portions defining a terminal slot therein, the terminal slot adapted to permit passage of the male terminal of the electrode; and
a contact tab having tab portions defining an elongated tapered opening in general alignment with the terminal slot of the base member and arranged for at least partial reception of the male terminal of the electrode;
whereby, upon traversing movement of the male terminal within the terminal slot, the male terminal is engaged by the tab portions defining the tapered opening of the spring clip to facilitate coupling of the male terminal with the connector housing.

16. The biomedical electrode according to claim 15 wherein the tab portions of the contact tab are deflected in a direction away from the base member to facilitate the at least partial reception of the male terminal of the electrode.

17. The biomedical electrode according to claim 15 wherein the tapered opening of the contact tab defines a first portion having a relatively enlarged internal dimension and a second portion having a relatively small internal dimension whereby, upon the traversing movement of the male terminal within the terminal slot, the male terminal is engaged by the tab portions adjacent the second portion of the tapered opening of the contact tab.

18. The biomedical electrode according to claim 17 wherein the tab portions adjacent the second portion of the tapered opening of the contact tab are adapted to engage an enlarged head of the male terminal of the electrode.

19. The biomedical electrode according to claim 18 wherein the contact tab is sufficiently resilient and is adapted to engage the enlarged head of the male terminal of the electrode when the male terminal is in the second portion of the tapered opening of the contact tab to thereby draw the enlarged head and electrode base toward the base member of the connector housing.

20. A biomedical electrode connector for coupling with a biomedical electrode including an electrode base and a male terminal projecting from the electrode base, the electrode connector comprising:
a connector housing having electrical contact material adapted to establish an electrical coupling relation with an electrical lead wire, the connector housing including:
a lower member adapted to be positioned adjacent the electrode;
an electrode contact tab extending in cantilever relation within the lower member and being at least partially defined by a relief slot within the lower member, the relief slot at least partially circumscribing the electrode contact tab, the electrode contact tab having internal surface portions defining a terminal slot therein, the terminal slot having a first slot portion defining a first internal dimension adapted to receive the male terminal of the electrode and a second slot portion defining a second internal dimension less than the first internal dimension;
whereby, upon traversing movement of the male terminal within the terminal slot of the electrode contact tab from the first slot portion to the second slot portion, the electrode tab is permitted to flex due, at least in part to the relief slot, to permit passage of the male terminal to facilitate retention of the male terminal within the second slot portion.

21. The biomedical electrode according to claim 20 wherein the electrode contact tab includes a ramp surface adapted to draw the male terminal within the connector housing.

22. The biomedical electrode according to claim 21 wherein the ramp surface is disposed adjacent an intersection of the first slot portion and the second slot portion.

23. The biomedical electrode according to claim 22 wherein the electrode contact tab is adapted to engage an enlarged head of the male terminal of the electrode when the male terminal moves within the second slot portion of the terminal slot of the electrode contact tab.

24. The biomedical electrode according to claim 20 wherein the connector housing includes an upper member, the male terminal contacting the upper member when the male terminal moves within the second slot portion of the terminal slot of the electrode contact tab.

25. The biomedical electrode according to claim 24 wherein the upper member includes a contacting segment in general alignment with the second slot portion of the contact tab, the contacting segment depending toward the lower member and dimensioned to engage an upper surface of the male terminal to facilitate coupling of the electrode with the connector housing.

* * * * *